(12) United States Patent
Dolnik

(10) Patent No.: US 7,799,195 B2
(45) Date of Patent: Sep. 21, 2010

(54) NEUTRAL POLYSACCHARIDE WALL COATING FOR ELECTROPHORETIC SEPARATIONS IN CAPILLARIES AND MICROCHANNELS

(76) Inventor: Vladislav Dolnik, 409 Kent Dr., Mountain View, CA (US) 94043

( * ) Notice: Subject to any disclaimer, the term of this patent is extended or adjusted under 35 U.S.C. 154(b) by 1001 days.

(21) Appl. No.: 11/162,255

(22) Filed: Sep. 2, 2005

(65) Prior Publication Data
US 2007/0051628 A1    Mar. 8, 2007

(51) Int. Cl.
*G01N 27/453* (2006.01)
(52) U.S. Cl. .................. 204/469; 204/605; 204/606
(58) Field of Classification Search ............ 204/469, 204/600–606, 450–456
See application file for complete search history.

(56) References Cited

U.S. PATENT DOCUMENTS

| 4,332,894 | A |   | 6/1982  | Whistler .................. 435/99 |
| 4,680,201 | A |   | 7/1987  | Hjerten ................. 204/601 |
| 5,074,982 | A |   | 12/1991 | Dolnik et al. ........... 204/454 |
| 5,143,753 | A |   | 9/1992  | Dolnik .................. 204/601 |
| 5,314,593 | A | * | 5/1994  | Swedberg ............... 204/601 |
| 5,332,481 | A | * | 7/1994  | Guttman ................. 204/455 |
| 5,364,520 | A | * | 11/1994 | Okuyama et al. ......... 204/605 |
| 5,502,169 | A |   | 3/1996  | Schomburg ............. 204/454 |
| 5,814,199 | A | * | 9/1998  | Dasgupta ............... 204/453 |
| 6,074,542 | A |   | 6/2000  | Dolnik et al. ........... 204/454 |
| 6,416,643 | B1 | * | 7/2002  | Henry et al. ............ 204/452 |
| 2002/0049184 | A1 |   | 4/2002  | Dolnik et al. ........... 536/114 |

FOREIGN PATENT DOCUMENTS

JP        05288717 A  * 11/1993

OTHER PUBLICATIONS

The JPO computer English language translation of Norio et al. JP 05-288717 A, patent published Nov. 2, 1993.*
Agilent G1600A Capillary Electrophoresis System Service Guide, published 2001.*
Ullsten et al. "Quaternary ammonium substituted agarose as surface coating for capillary electrophoresis," Analyst, 2004, 129, 410-415.*
Huang et al., "Hydrogel polymer Coatings for Capillary Electrophoretic Separation of Proteins," J. Microl. Sep. 4, 491-496 (1992).*
Huang et al., "Hydrolytically stable cellulose-derivative coatings for capillary electrophoresis of peptides, proteins and glycoconjugates," Electrophoresis, 1995, 16, 396-401.*
Handbook of Hydrocolloids, Phillips, G. O. ed., Woodhead Publishing, 2000, pp. 1-19.*

* cited by examiner

*Primary Examiner*—Alex Noguerola

(57) ABSTRACT

The present invention describes a method of preparation of a permanent neutral wall coating made of thermally immobilized polysaccharides. The coating suppresses electroosmotic flow and adsorption on the wall under acidic, neutral, and basic conditions in capillary electrophoresis.

12 Claims, 5 Drawing Sheets

NEUTRAL POLYSACCHARIDE WALL COATING FOR ELECTROPHORETIC SEPARATIONS IN CAPILLARIES AND MICROCHANNELS

REFERENCES CITED

U.S. Patent Documents

1) Hjertén, S., Coating for electrophoresis tube. U.S. Pat. No. 4,680,201, 1987.
2) Novotny, M. V.; Cobb, K. A., and Dolnik, V., Suppression of electroosmosis with hydrolytically stable coatings. U.S. Pat. No. 5,074,982, 1990.
3) Novotny, M. V.; Cobb, K. A., and Dolnik, V., Suppression of electroosmosis with hydrolytically stable coatings. U.S. Pat. No. 5,143,753, 1991.
4) Dolnik, V. and Chiari, M., Compounds for molecular separations. U.S. Pat. No. 6,074,542, 2000.
5) Schomburg, G. and Gilges, M., Deactivation of the inner surfaces of capillaries. U.S. Pat. No. 5,502,169, 1996.
6) V. Dolník, W. A. Gurske, and A. Padua: Solution of galactomannans as a sieving matrix in capillary electrophoresis. U.S. Patent Application 20020049184, Sep. 5, 2001.
7) Whistler R., Conversion of Guar Gum to Gel-Forming Polysaccharides by the Action of Alpha-Galactosidase. U.S. Pat. No. 4,332,894, 1982.

Other References

1) Maier, H., Anderson, M., Karl, C., Magnus on, K., in: Whistler, R. L., BeMiller, J. N. (Eds.), *Industrial Gums. Polysaccharides and Their Derivatives*, Academic Press, San Diego 1993, pp. 181-226.
2) Dolník, V., Gurske, W. A. and Padua, A.: Galactomannans as a sieving matrix in capillary electrophoresis. *Electrophoresis* 2001, 22, 707-719.
3) Williams, B. A. and Vigh, G. Determination of accurate electroosmotic mobility and analyte effective mobility values in the presence of charged interacting agents in capillary electrophoresis. *Anal. Chem.* 1997. 69, 4445-4451.
4) Liu, Q., Lin, F., Hartwick, R. A. Capillary zone electrophoretic separation of basic proteins and drugs using guaran as a buffer modifier. *Chromatographia* 1998, 47, 219-224.
5) Belder, D. Deege, A., Husmann, H., Kohler, F., and Ludwig, M. Cross-linked poly(vinyl alcohol) as permanent hydrophilic column coating for capillary electrophoresis. *Electrophoresis.* 2001; 22, 3813-3818.
6) Shen, Y. and Smith, R. D. High-resolution capillary isoelectric focusing of proteins using highly hydrophilic-substituted cellulose-coated capillaries. *J. Microcol. Sep.* 2000; 12, 135-141.
7) Slais, K., Friedl, Z. Low-Molecular-Mass pI Markers for Isoelectric Focusing. *J. Chromatogr. A* 1994, 661, 249-256.
8) Gilges, M., Kleemiss, M. H., Schomburg, G., Capillary zone electrophoresis separations of basic and acidic proteins using poly(vinyl alcohol) coatings in fused silica capillaries. *Anal. Chem.* 1994, 66, 2038-2046.
9) Belder, D. Deege, A., Kohler, F., and Ludwig, M. Poly(vinyl alcohol)-coated microfluidic devices for high-performance microchip electrophoresis. *Electrophoresis.* 2002; 23, 3567-3573.
10) Belder, D., and Ludwig, M. Surface modification in microchip electrophoresis. *Electrophoresis.* 2003; 24, 3595-3606.
11) Becker, H., Locascio, L. E., Polymer microfluidic devices. *Talanta* 2002, 56, 267-287.

FIELD OF THE INVENTION

The present invention generally relates to surface treatment, films and coatings, and more particularly coatings for chromatography and electrophoresis in capillaries and microchannels. Specifically, the invention is directed to wall coatings in capillary electrophoresis to reduce electroosmotic flow and adsorption of analytes on the wall.

BACKGROUND OF THE INVENTION

Capillary electrophoresis has achieved a remarkably rapid development from its introduction in the early 1980s. This technique miniaturizes the electrophoretic process and presents significant advantages over traditional slab gel electrophoretic techniques. While fused silica capillaries are the most frequently used separation format, the method was also transferred to microchips (Belder, D., and Ludwig, M. Surface modification in microchip electrophoresis. *Electrophoresis.* 2003; 24, 3595-3606, Becker, H., Locascio, L. E., Polymer microfluidic devices. *Talanta* 2002, 56, 267-287.) Most of materials used to prepare separation channels or capillaries for capillary electrophoresis (CE) contain ionizable groups on their surface that are responsible for so-called electrokinetic potential or $\zeta$-potential. This potential is a cause of electroosmotic flow (EOF). The presence of EOF and especially its uneven distribution along the electrophoretic capillary or channel causes disturbances called eddy migration and loss of resolution during electrophoretic separation. To suppress EOF, a good wall coating eliminates $\zeta$-potential at the wall and/or increases viscosity inside the electric double layer. To reduce $\zeta$-potential, the coating may react with charged groups incorporated in the wall (silanol groups in the case of fused silica capillary). To some extent, compounds with an opposite charge than the ionizable groups of the wall can be also used to titrate $\zeta$-potential.

A number of various wall coatings have been proposed and developed to eliminate EOF and adsorption of analytes in fused silica capillaries. A vast majority of them merely reduced EOF and did not eliminate it completely. Frequently a dynamic wall coating was formed by simply adding an active ingredient to the background electrolyte. It adsorbed on the wall and reduced capillary surface charge and/or viscosity of solution in the electric double layer. Dynamic wall coatings are popular because of the simplicity of their preparation. However, they do not eliminate electroosmotic flow completely. Among many dynamic coatings, a dynamic coating based on guaran has been developed (Liu, Q., Lin, F., Hartwick, R. A. Capillary zone electrophoretic separation of basic proteins and drugs using guaran as a buffer modifier. *Chromatographia* 1998, 47, 219-224).

To eliminate EOF completely, static wall coatings have to be applied. Typically, a static wall coating is made of two layers: an intermediate layer and a hydrophilic polymer layer. A bifunctional reagent that reacts with both the capillary surface and functional groups of the polymer molecule usually forms the intermediate layer. The first polymer used for the preparation of a static wall coating was a linear polyacrylamide attached to the fused silica capillary wall by γ-methacryloxypropyltrimethoxysilane (Hjertén, S., Coating for electrophoresis tube. U.S. Pat. No. 4,680,201). More hydrolytically stable coating was obtained when polyacrylamide was attached to the silica wall by using a Grignard reagent with an olefinic moiety, e.g., vinylmagnesium bromide after activating silanol groups by a reaction with thionyl chloride (Novotny, M. V.; Cobb, K. A., and Dolnik, V., Suppression of electroosmosis with hydrolytically stable coatings. U.S. Pat. No. 5,074,982; Novotny, M. V.; Cobb, K. A., and Dolnik, V., Suppression of electroosmosis with hydrolytically stable coatings. U.S. Pat. No. 5,143,753). Polyacrylamide is, however, hydrolytically unstable at high pH and hydrolyzes forming poly(acrylic acid). The presence of carboxylic groups leads to generation of ζ-potential on the wall and to an increase of EOF. A more stable wall coating is usually obtained if acrylamide is replaced with its derivative having some substituents on nitrogen (Dolnik, V. and Chiari, M., Compounds for molecular separations. U.S. Pat. No. 6,074,542).

Thermal immobilization of a polymer on a capillary wall is another way how to anchor a polymer on the capillary wall. Schomburg and coworkers proposed a poly(vinyl alcohol) (PVA) coating fixed thermally to the wall by heating the capillary at 140.degree.C. They assumed that formation of a permanent PVA coating was based on PVA insolubility in water after the thermal treatment and expected PVA to form semi-crystalline highly associated structures, which were not covalently bound to the fused silica capillary. PVA molecules became more strongly associated by hydrogen bridges and water molecules could not penetrate microcrystalline domains. The authors expressed their opinion that this was a unique property of PVA. In the pH range of 5-9, the PVA coating did not, however, completely eliminate EOF and the coated capillaries exhibited a pH-independent electroosmotic mobility of $1.2 \times 10^{-9}$ $m^2V^{-1}s^{-1}$ as measured in 20 mM sodium phosphate (Schomburg, G. and Gilges, M., Deactivation of the inner surfaces of capillaries. U.S. Pat. No. 5,502,169). The procedure was further modified to make a PVA wall coating on a glass microchip. A newly introduced PVA coating crosslinked with glutaraldehyde should improve the stability of the coating. No heating is necessary, just drying is sufficient to provide a stable wall coating (Belder, D., Deege, A., Husmann, H., Kohler, F., and Ludwig, M. Cross-linked poly(vinyl alcohol) as permanent hydrophilic column coating for capillary electrophoresis. *Electrophoresis*. 2001; 22, 3813-3818). Thermal immobilization was also applied to hydroxyethyl cellulose (HEC) and hydroxypropyl cellulose (HPC) (Shen, Y. and Smith, R. D. High-resolution capillary isoelectric focusing of proteins using highly hydrophilic-substituted cellulose-coated capillaries. *J. Microcol. Sep.* 2000; 12, 135-141). The authors found that the wall coating was stable if the silica capillaries were heated at 140° C. for 20 min rather than just being dried at room temperature for 4 days. From this observation they concluded that a chemical reaction must have occurred between cellulose derivatives and fused silica capillary inner wall.

There are several types of galactomannans, a class of linear polysaccharides with 1,4 linked β-D-mannopyranosyl units and 1,6-linked α-D-galactopyranosyl side groups (Dolník, V., Gurske, W. A. and Padua, A.: Galactomannans as a sieving matrix in capillary electrophoresis. *Electrophoresis* 2001, 22, 707-719). The four most important galactomannans are locust bean gum, tara gum, guar gum (guaran), and fenugreek gum, which differ by the frequency of galactosyl side group attachment to the polymannose. The ratio of D-mannosyl to D-galactosyl units is approximately 3.8:1 for locust bean gum, 3:1 for tara gum, 1.8:1 for guar gum, and about 1:1 for fenugreek gum. Locust bean gum, guar gum, and tara gum are commercially produced and have various applications in the food industry and as an additive to fracturing fluids in the petroleum industry. Guar gum is obtained from the endosperm portion of the legume seed (*Cyamopsis tetragonoloba*) that grows mainly on the Indian subcontinent and in some parts of Texas and Oklahoma. Typical guar gum contains 75-85% of galactomannan, 8-14% water, 5-6% proteins, 2-3% fiber, and 0.5-1% ash. Guar gum shows an excellent resistance to shear degradation (Maier, H., Anderson, M., Karl, C., Magnus on, K., in: Whistler, R. L., BeMiller, J. N. (Eds.), *Industrial Gums. Polysaccharides and Their Derivatives*, Academic Press, San Diego 1993, pp. 181-226).

Solubility of polysaccharides and viscosity of their solutions significantly depends on branching of polysaccharide chains. Whereas cellulose is insoluble in water, as numerous hydrogen bridges between closely placed linear polysaccharide chains prevent its solubilization, highly branched polysaccharides, such as dextran, can be easily and quickly dissolved in water. When cellulose is derivatized with hydroxyalkyl groups, their presence keep polysaccharide chains apart and cellulose derivative becomes soluble in water (Whistler, R. L., BeMiller, J. N. (Eds.), *Industrial Gums. Polysaccharides and Their Derivatives*, Academic Press, San Diego 1993). Similarly, locust bean gum, where polymannose backbone fibers are kept apart only by 1 galactose side group per about 3.8 mannose units, is less soluble in water than, e.g., guar gum, where polymannose backbone fibers are kept apart by 1 galactose side group per about 1.8 mannose units (Maier, H., Anderson, M., Karl, C., Magnus on, K., in: Whistler, R. L., BeMiller, J. N. (Eds.), *Industrial Gums. Polysaccharides and Their Derivatives*, Academic Press, San Diego 1993, pp. 181-226). Solubility of polysaccharides can be reduced by enzymatic reaction, when side chains and side groups are hydrolytically cleaved from a polysaccharide backbone (Whistler R., Conversion of Guar Gum to Gel-Forming Polysaccharides by the Action of Alpha-Galactosidase. U.S. Pat. No. 4,332,894, 1982).

SUMMARY OF THE INVENTION

The present invention is useful as a capillary coating that satisfies the above objectives. The polysaccharide coating described here eliminates electroosmotic flow and reduces adsorption on the capillary wall. The coating is stable for at least 48 hours at pH 10.3.

The present invention is also a method of preparing said coating and using this coating to cover the interior of a capillary tube.

DETAILED DESCRIPTION OF THE INVENTION

Figure 1:
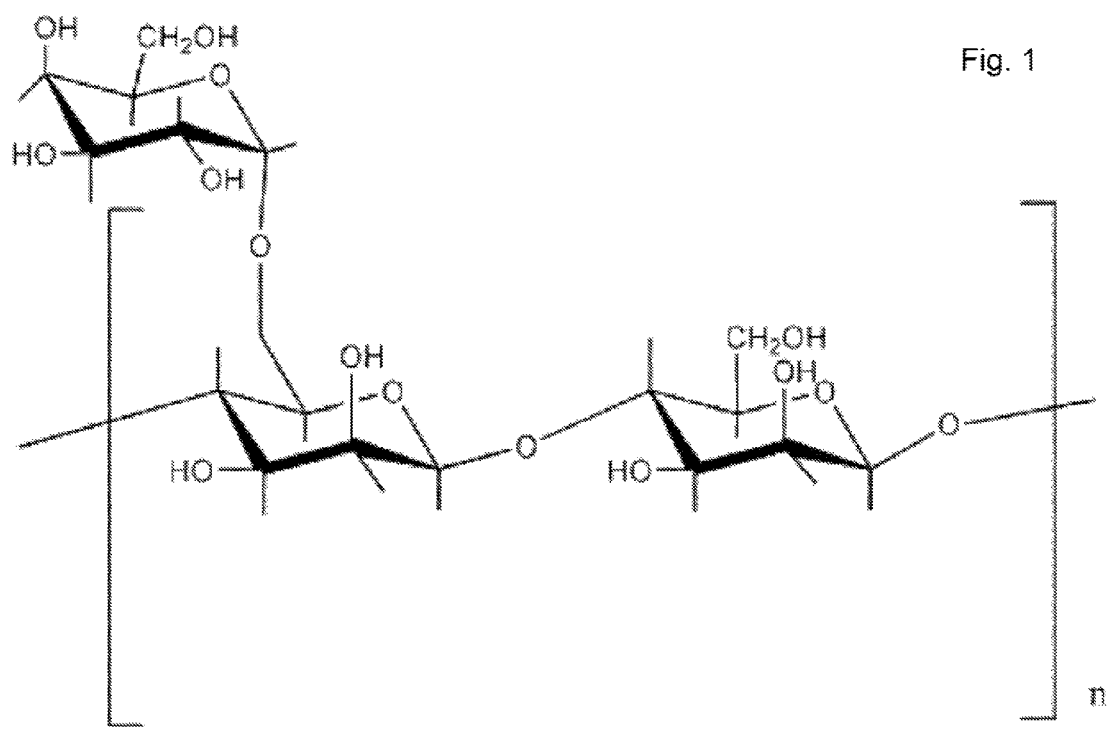
FIG. 1 represents the idealized structure of guaran.

Here we disclose a separation column for electrophoretic separation of molecules, realized as a channel in a body; wherein
- said body made as a capillary or block of an electrically insulating material selected from the group consisting of fused silica, glass, poly(methyl methacrylate), polycarbonate, poly(tetrafluoroethylene), and cyclic polyolefins;
- said separation column having a polysaccharide coating permanently attached to the interior surface of said separation column;
- said polysaccharide coating comprising at least one permanent layer made of one or more polysaccharides selected from the group of polysaccharides consisting of: locust bean gum, tara gum, guar gum, hydroxyisopropyl guaran, fenugreek gum, konjac, pullulan, pustullan, curdlan, laminaran, tragacanth gum, amylose, schyzophyllan, nigeran, and scleroglucan;
- said polysaccharide coating produced by thermal immobilization of one or more said polysaccharides at temperature between about 100° C. and about 160° C.

Further we disclose the separation column for electrophoretic separation of molecules contains a polysaccharide coating that is thermally immobilized in a protective atmosphere of dry gas selected form the group consisting of: nitrogen, helium, and argon.

Further we disclose the he separation column for electrophoretic separation of molecules, wherein said polysaccharide coating is thermally immobilized at pressure between about 0 ton and about 700 torr.

Further we disclose the he separation column for electrophoretic separation of molecules, wherein said polysaccharide coating is thermally immobilized at pressure between about 0 ton and about 200 torr.

Further we disclose the he separation column for electrophoretic separation of molecules, wherein said polysaccharide coating is thermally immobilized at pressure between about 0 ton and about 2 torr.

Further we disclose the a method for preparation of a separation column, comprising steps:
a) flushing said separation column with about 0.1 mL thionyl chloride;
b) flushing said separation column with distilled water;
c) filling said separation column with a polysaccharide solution comprising from about 0.5 g/L to about 20 g/L polysaccharide selected from the group consisting of: locust bean gum, tara gum, guar gum, hydroxyisopropyl guaran, fenugreek gum, konjac, pullulan, pustullan, curdlan, laminaran, tragacanth gum, amylose, schyzophyllan, nigeran, and scleroglucan;
d) incubating said separation column filled with said polysaccharide solution at temperature between about 100° C. and about 160° C. for the time interval between about 5 minutes and about 30 minutes, at pressure in the range between about 0 ton and about 2 ton.

We also disclose the separation column for electrophoretic separation of molecules, wherein side branches and side carbohydrate units of said polysaccharide in said branched polysaccharide coating are cleaved from the polysaccharide backbone by a glycolytic enzyme.

Further we disclose the separation column for electrophoretic separation of molecules, wherein said branched polysaccharide is selected from the group consisting of locust bean gum, tara gum, guar gum, and fenugreek gum; and said glycolytic enzyme is $\alpha$-galactosidase.

Further we disclose the separation column for electrophoretic separation of molecules, wherein said polysaccharide is selected from the group consisting of amylose, nigeran, and pullulan; and said glycolytic enzyme is $\alpha$-glucosidase.

Further we disclose the separation column for electrophoretic separation of molecules, wherein said polysaccharide is selected from the group consisting of scleroglucan, schyzophyllan, pustullan, laminaran, and curdlan; and said glycolytic enzyme is $\beta$-glucosidase.

EXAMPLES

Example 1

Wall Coating Preparation by Thermal Immobilization of Guaran 3 m piece of fused silica capillary 75 μm ID, 360 μm OD was flushed with 0.1 mL thionyl chloride under pressure of 500 psi to clean the inner surface of the capillary. Then the capillary was filled with 1 g/L guaran at pressure of 1000 psi. Guaran (FIG. 1) solution was prepared by dissolving a purified guaran (Jaguar 2229, Rhodia, Hercules, Pa.) in deionized water and filtered through 0.2 μm nylon syringe filter. Crude guaran was previously purified by treatment with ion exchanger Source 30Q (Pharmacia, Uppsala, Sweden) and Amberlite MB-150 (Sigma, St. Louis, Mo.) followed by ion exchange treatment on Source 30S (Pharmacia, Uppsala, Sweden) and by precipitation with acetone (V. Dolnik, W. A. Gurske, and A. Padua: Solution of galactomannans as a sieving matrix in capillary electrophoresis. U.S. Patent Application 20020049184, Sep. 5, 2001). The solution of guaran was left to flow through the capillary for 20 minutes. Then the capillary was flushed with nitrogen filtered through 0.2 μm nylon syringe filter at 1000 psi and after the capillary was emptied it was dried by flowing nitrogen through it at 100 psi. After a few minutes, the nitrogen flow was reduced to 20 psi and the capillary was placed in the oven heated to 102-105° C. for 30 minutes. After 30 minutes the capillary was cooled to room temperature and the nitrogen flow is stopped. The process can be repeated (without thionyl chloride treatment) providing multiple layer capillary coating.

Figure 2:
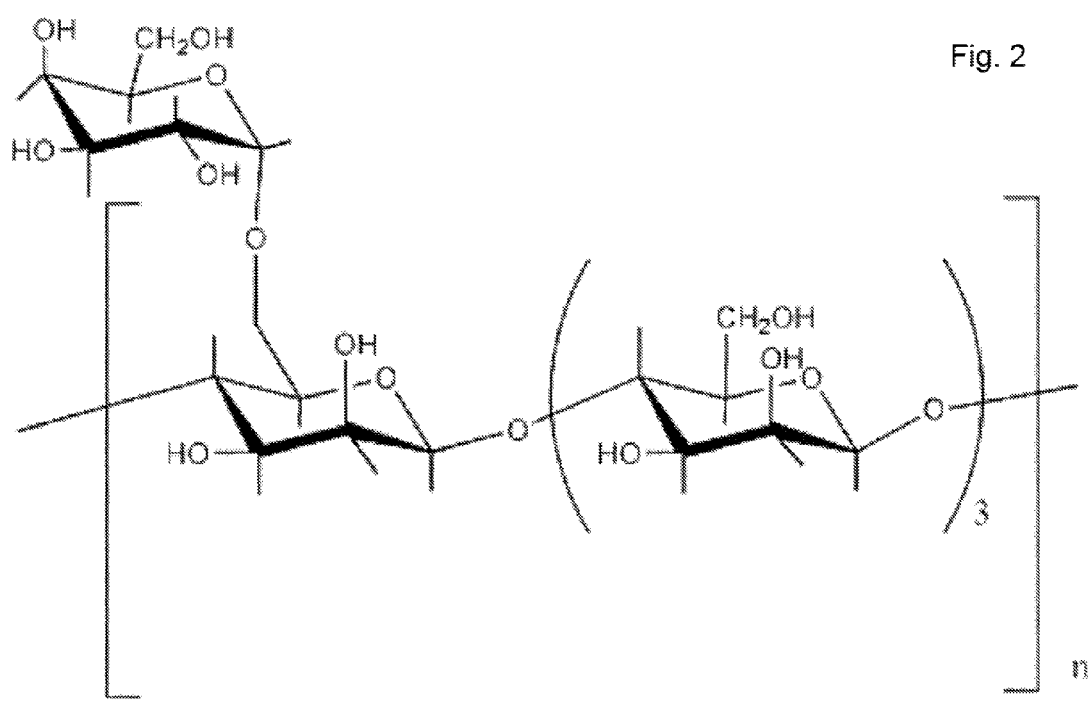
FIG. 2 shows the idealized structure of locust bean gum.

Similarly other polysaccharides can be used to make a hydrophilic neutral wall coating including locust bean gum (FIG. 2), tara gum, fenugreek gum, scleroglucan, pullulan, and konjac, to name a few. In this way a hydrophilic film is prepared that may have other applications including homogenous lower layer for attachment of nucleic acid or proteins in preparation of microarrays.

Example 2

Electroosmotic Mobility of Guaran Wall Coating and

Electroosmotic mobility ($\mu_{EEO}$) of the prepared wall coating was measured in a 335 mm long capillary with effective length of 250 mm using equimolar solution of tris(hydroxymethyl)aminomethane (Tris) and N-(2-hydroxyethyl)piperazine-N'-(2-ethanesulfonic acid) (HEPES) as ackground electrolyte (BGE) and 100 mM nicotinamide or 1 g/L hydroxyethyl methacrylate as a neutral marker. First a band of the marker was injected as a 2 s pulse at 50 mbar to the capillary inlet and was moved forward by pumping BGE electrolyte into capillary for 35 s at 50 mbar. Then another 2-s pulse of the neutral marker was injected at 50 mbar and moved forward into capillary by pumping BGE at 50 mbar for 35 s. The −10 kV voltage was applied for 180 s and a 3$^{rd}$ pulse of the neutral marker (2 s at 50 mbar) was introduced into the capillary Then the all three bands of the neutral marker were pumped through the capillary at pressure of 50 mbar, while measuring absorption at 214 nm. Migration times of these three peaks were measured and used to calculate electroosmotic mobility (Williams, B. A. and Vigh, G., Determination of accurate electroosmotic mobility and analyte effective mobility values in the presence of charged interacting agents in capillary electrophoresis. *Anal. Chem.* 1997, 69, 4445-4451).

By using this method we measured electroosmotic mobility of the prepared capillaries. For high-quality coating that significantly suppresses EOF ($\mu_{EEO}$) below 10−9 m$^2$V$^{-1}$s$^{-1}$), it is necessary to apply high voltage during measurement for extended period of time to achieve good reproducibility.

Example 3

Capillary Zone Electrophoresis of Acid Protein Mixture

Figure 3:
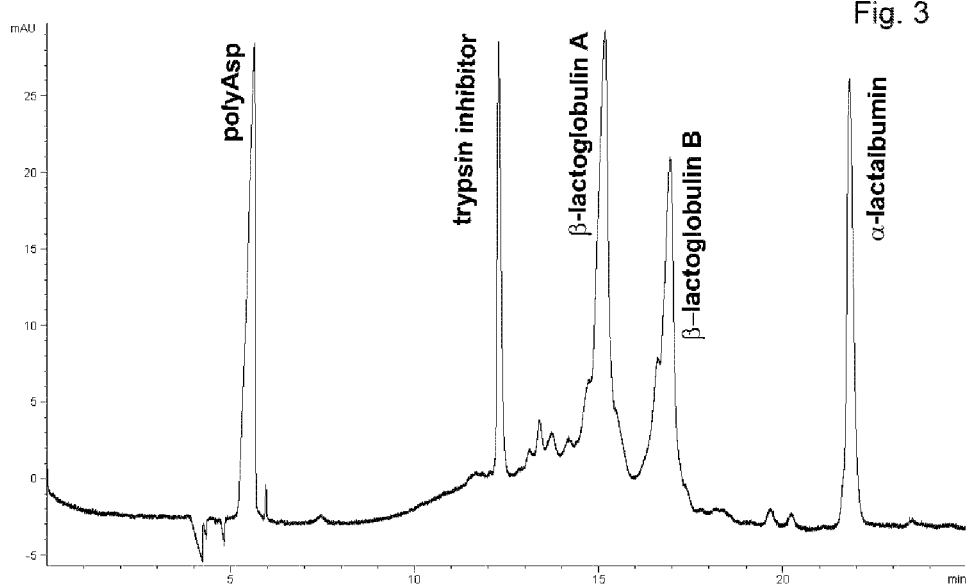
FIG. 3 is an electropherogram of a model acidic protein mixture in guaran-coated capillary. Capillary: 1(total)=335 mm, 1(effective)=250 mm, ID=50 μm, OD=360 μm. BGE: 100 mM Tris-HEPES; voltage: −10 kV, injection: 30 mbar 3 s. Sample: 10 g/L polyglutamate, 4 g/L trypsin inhibitor, 8 g/L .alpha.-lactoglobulin, 1 g/L .beta.-lactalbumin.

Quality of the prepared guaran wall coating was tested by CZE of model acid proteins in the guaran-coated capillary. The total length of the capillary was 335 mm, the effective length of the capillary was 250 mm. The capillary had ID 50 μm and OD 360 μm. For a CE separation of acid proteins, background electrolyte containing 100 mM Tris and 100 mM HEPES, pH 8.1 was used and a constant voltage of −10 kV was applied. The sample containing 10 g/L polyGlu, 4 g/L trypsin inhibitor, 8 g/L .beta.-lactoglobulin, 1 g/L .alpha.-lactalbumin in water was injected hydrodynamically applying pressure of 30 mbar for 3 s. The peaks were detected by measuring UV absorption at 214 nm. All five model proteins were separated in less than 25 minutes (FIG. 3).

Example 4

Capillary Zone Electrophoresis of Basic Protein Mixture

Figure 4:
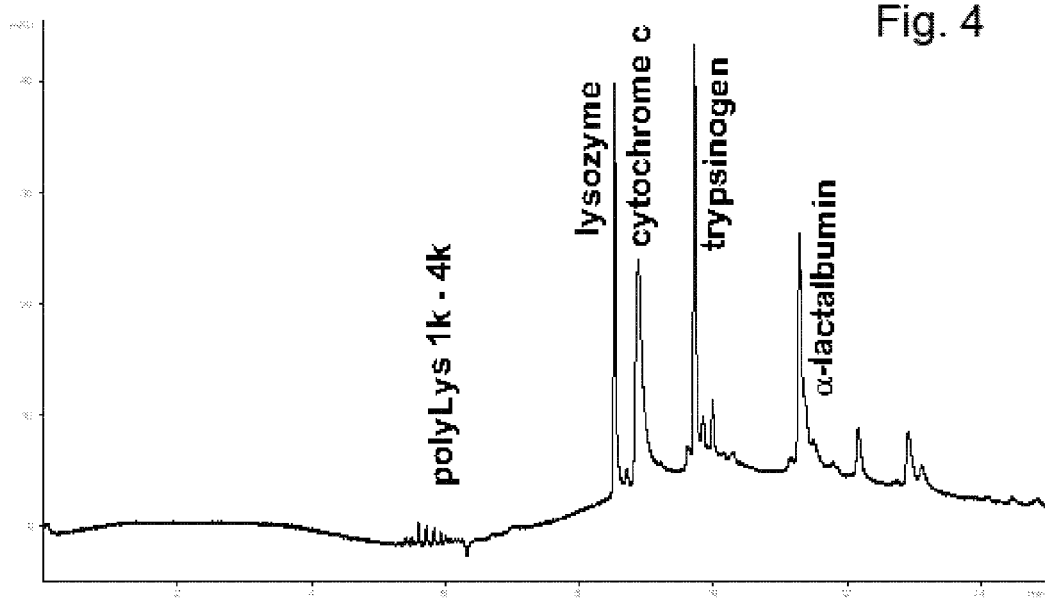
FIG. 4 is an electropherogram of a model basic protein mixture in guaran-coated capillary. Capillary: 1(total)=335 mm, 1(effective)=250 mm, ID=75 μm, OD=360 μm. BGE: 100 mM .beta.-alanine-citric acid; voltage: −10 kV, injection: 30 mbar 3 s. Sample: 2 g/L polylysine, lysozyme, cytochrome c, trypsinogen, and .alpha.-lactalbumin.

Quality of the prepared guaran wall coating was tested by CZE of model basic proteins in a guaran-coated capillary. The total length of the capillary was 335 mm, the effective length of the capillary was 250 mm. The capillary had ID 75 μm and OD 360 μm. For a CE separation of acid proteins, background electrolyte containing 100 mM .beta.-alanine and 100 mM citric acid, pH 3.3 was used and a constant voltage of −10 kV was applied. The sample containing 2 g/L polylysine, lysozyme, cytochrome c, trypsinogen, and .alpha.-lactalbumin in water was injected hydrodynamically applying pressure of 30 mbar for 3 s. The peaks were detected by measuring UV absorption at 214 nm (FIG. 4).

Example 5

Capillary Isoelectric Focusing of pI Standards in Guaran-Coated Capillary

Figure 5:
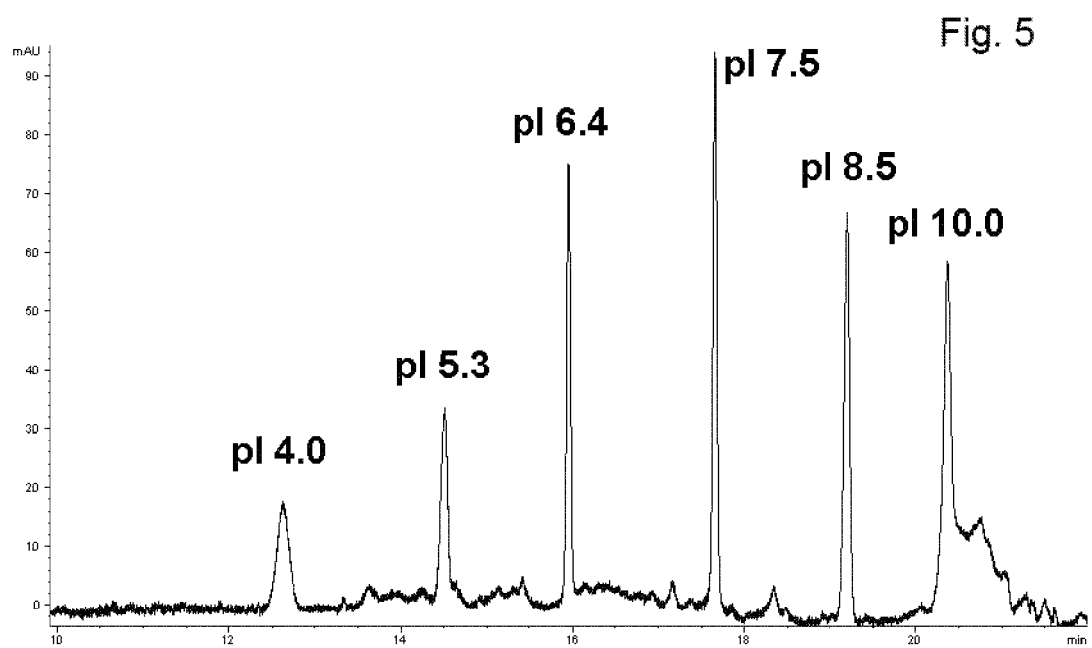
FIG. 5 shows isoelectric focusing of synthetic pI standards in capillary coated with guaran. Capillary: 1(total)=335 mm, 1(effective)=250 mm, ID=75 μm, OD=360 μm. Anolyte: 20 mM citric acid, catholyte: 40 mM NaOH. Capillary filled with 1% Ampholines 3.5-10, 0.1% purified Synergel, 25 mM BisTris Propane. Focusing: 20 kV 8 min, mobilization: 100 mbar, 20 kV.

Utility of guaran-coated capillary for capillary isoelectric focusing was tested by isoelectric focusing of colored synthetic pI markers (FIG. 5). The capillary had ID 50 μm and OD 360 μm. For the focusing step, anolyte containing 20 mM citric acid and catholyte containing 40 mM NaOH were used. The capillary was filled with 1% Ampholines (pI range 3.5-10), 0.1% purified Synergel, and 25 mM BisTris Propane. In the focusing step 20 kV was applied for 8 min, then the focused zones were mobilized by applying pressure of 100 mbar, at 20 kV. As a sample, a mixture of six synthetic pI markers having pI 4.0, 5.3, 6.4, 7.5, 8.5, and 10.0 (Šlais, K., Friedl, Z. Low-Molecular-Mass pI Markers for Isoelectric Focusing. *Journal of Chromatography A* 1994, 661, 249-256.) were injected. Migration times of the pI standards were linearly proportional to pI. In this particular case the relationship could have been expressed by the equation $$t_m = 7.50 + 0.51 pI$$

where $t_m$ is migration time and pI isoelectric point.

What is claimed is:

1. A separation column for electrophoretic separation of molecules, realized as a channel in a body;
    said body made of an electrically insulating material selected from the group consisting of fused silica, glass, poly(methyl methacrylate), polycarbonate, poly(tetrafluoroethylene), and cyclic polyolefins;
    said separation column having a polysaccharide coating permanently attached to the interior surface of said separation column;
    said polysaccharide coating comprising at least one permanent layer made of one or more polysaccharides selected from the group of polysaccharides consisting of: locust bean gum, tara gum, guar gum, hydroxyisopropyl guaran, fenugreek gum, konjac, pullulan, pustulan, curdlan, laminaran, tragacanth gum, amylose, schyzophyllan, nigeran, and scleroglucan;
    said polysaccharide coating produced by thermal immobilization of one or more said polysaccharides at temperature between about 100° C. and about 160° C. for about 5 to about 30 minutes.

2. The separation column for electrophoretic separation of molecules as recited in claim 1, wherein said polysaccharide coating is thermally immobilized in a protective atmosphere comprising at least 99.9 percent dry gas selected form the group of gases consisting of nitrogen, helium, and argon.

3. The column for electrophoretic separation of molecules as recited in claim 1, wherein said thermal immobilization is performed in vacuum at pressure between about 0 torr and about 700 ton.

4. The column for electrophoretic separation of molecules as recited in claim 1, wherein said thermal immobilization is performed in vacuum at pressure between about 0 ton and about 200 ton.

5. The column for electrophoretic separation of molecules as recited in claim 1, wherein thermal immobilization is performed in vacuum at pressure between about 0 ton and about 2 ton.

6. The column for electrophoretic separation of molecules as recited in claim 1, wherein said thermal immobilization is performed at temperature between about 102° C. and about 145° C. for about 20 to about 30 minutes.

7. A method for preparation of a separation column recited in claim 1, comprising steps:
    a) flushing said separation column with about 0.1 mL thionyl chloride;
    b) flushing said separation column with distilled water;
    c) flushing said separation column with a polysaccharide solution comprising from about 0.5 g/L to about 20 g/L polysaccharide selected from the group of polysaccharides consisting of: locust bean gum, tara gum, guar gum, hydroxyisopropyl guaran, fenugreek gum, konjak, pullulan, pustulan, curdlan, laminaran, tragacanth gum, amylose, schyzophyllan, nigeran, and scleroglucan;

d) incubating said separation column filled with said polysaccharide solution at temperature between about 100° C. and about 160° C. for the time interval between about 5 minutes and about 30 minutes, at pressure in the range between about 0 torr and about 2 ton.

8. A method for preparation of a separation column of claim 1, comprising steps:
   a) filling said separation column with a polysaccharide solution comprising about 5 g/L locust bean gum;
   d) incubating said separation column flushed with said polysaccharide solution at temperature about 135° C. for about 30 minutes at pressure between about 0 ton and about 2 ton.

9. The separation column for electrophoretic separation of molecules, as recited in claim 1, wherein side branches and side carbohydrate units of said polysaccharide in said polysaccharide coating are cleaved from the polysaccharide backbone by a glycolytic enzyme.

10. The separation column for electrophoretic separation of molecules, as recited in claim 9,
    wherein said polysaccharide is selected from the group of polysaccharides consisting of locust bean gum, tara gum, guar gum, and fenugreek gum; and said glycolytic enzyme is α-galactosidase.

11. The separation column for electrophoretic separation of molecules, as recited in claim 9, wherein
    said polysaccharide is selected from the group of polysaccharides consisting of amylose, dextran, nigeran, and pullulan; and
    said glycolytic enzyme is α-glucosidase.

12. The separation column for electrophoretic separation of molecules, as recited in claim 9, wherein
    said polysaccharide is selected from the group of polysaccharides consisting of scleroglucan, schyzophyllan, pustulan, laminaran, and curdlan; and
    said glycolytic enzyme is β-glucosidase.

* * * * *

UNITED STATES PATENT AND TRADEMARK OFFICE
CERTIFICATE OF CORRECTION

PATENT NO.      : 7,799,195 B2
APPLICATION NO. : 11/162255
DATED           : September 21, 2010
INVENTOR(S)     : Vladislav Dolnik Page 1 of 1

It is certified that error appears in the above-identified patent and that said Letters Patent is hereby corrected as shown below:

Column 8, line 42: "torr" instead of incorrect "ton";
Column 8, line 45: "torr" instead of incorrect "ton";
Column 8, line 46: "torr" instead of incorrect "ton";
Column 8, line 49: "torr" instead of incorrect "ton";
Column 8, line 50: "torr" instead of incorrect "ton";
Column 9, line 5: "torr" instead of incorrect "ton";
Column 9, line 13: "torr" instead of incorrect "ton";
Column 9, line 14: "torr" instead of incorrect "ton";

Signed and Sealed this
Twenty-eighth Day of June, 2011

David J. Kappos
*Director of the United States Patent and Trademark Office*